United States Patent [19]

Kessler et al.

[11] Patent Number: 4,808,292
[45] Date of Patent: Feb. 28, 1989

[54] ARRANGEMENT FOR STABILIZING A GAS-REFERENCE ELECTRODE

[76] Inventors: Manfred Kessler, Schlehenstr. 14; Jens Höper, Moorbachweg 28, both of 8520 Erlangen, Fed. Rep. of Germany

[21] Appl. No.: 923,725

[22] Filed: Oct. 24, 1986

[30] Foreign Application Priority Data

Oct. 24, 1985 [DE] Fed. Rep. of Germany ....... 3537919

[51] Int. Cl.⁴ ................ G01N 27/26; G01N 27/30; G01N 27/40; G01N 27/46
[52] U.S. Cl. ......................... 204/403; 204/406; 204/412; 204/416; 204/415; 204/418; 204/431; 204/432; 204/435
[58] Field of Search ............ 204/403, 415–418, 204/431–432, 435, 406, 411, 412, 1 Y, 1 K, 1 T

[56] References Cited

U.S. PATENT DOCUMENTS

| Re. 31,914 | 6/1985 | Oswin et al. | 204/1 K |
|---|---|---|---|
| 1,875,503 | 1/1931 | Rowland | 204/435 |
| 3,530,849 | 9/1970 | Watanabe | 204/435 |
| 4,263,115 | 4/1981 | Kessler | 204/416 |
| 4,432,366 | 2/1984 | Majules | 204/435 |

FOREIGN PATENT DOCUMENTS 0141178 5/1985 European Pat. Off. .
2730143 1/1979 Fed. Rep. of Germany .

Primary Examiner—John F. Niebling
Assistant Examiner—Ben C. Hsing
Attorney, Agent, or Firm—Michael J. Striker

[57] ABSTRACT

In a catheter or hollow needle type electrolytic measuring device having a measuring electrode and a gas reference electrode, an arrangement for stabilizing the operation of the gas reference electrode includes a lipophile membrane coating a part of the gas reference electrode which communicates with an electrolyte containing space. A source of gas, preferably in the form of another electrode which release gas at a constant rate from the electrolyte, is arranged in the space opposite the gas reference electrode.

24 Claims, 4 Drawing Sheets

F I G. 1
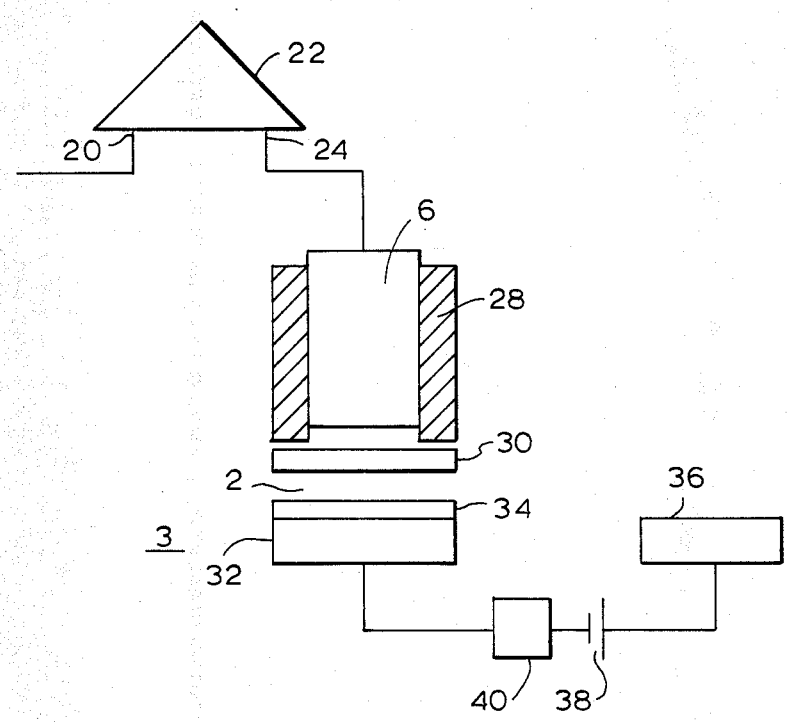

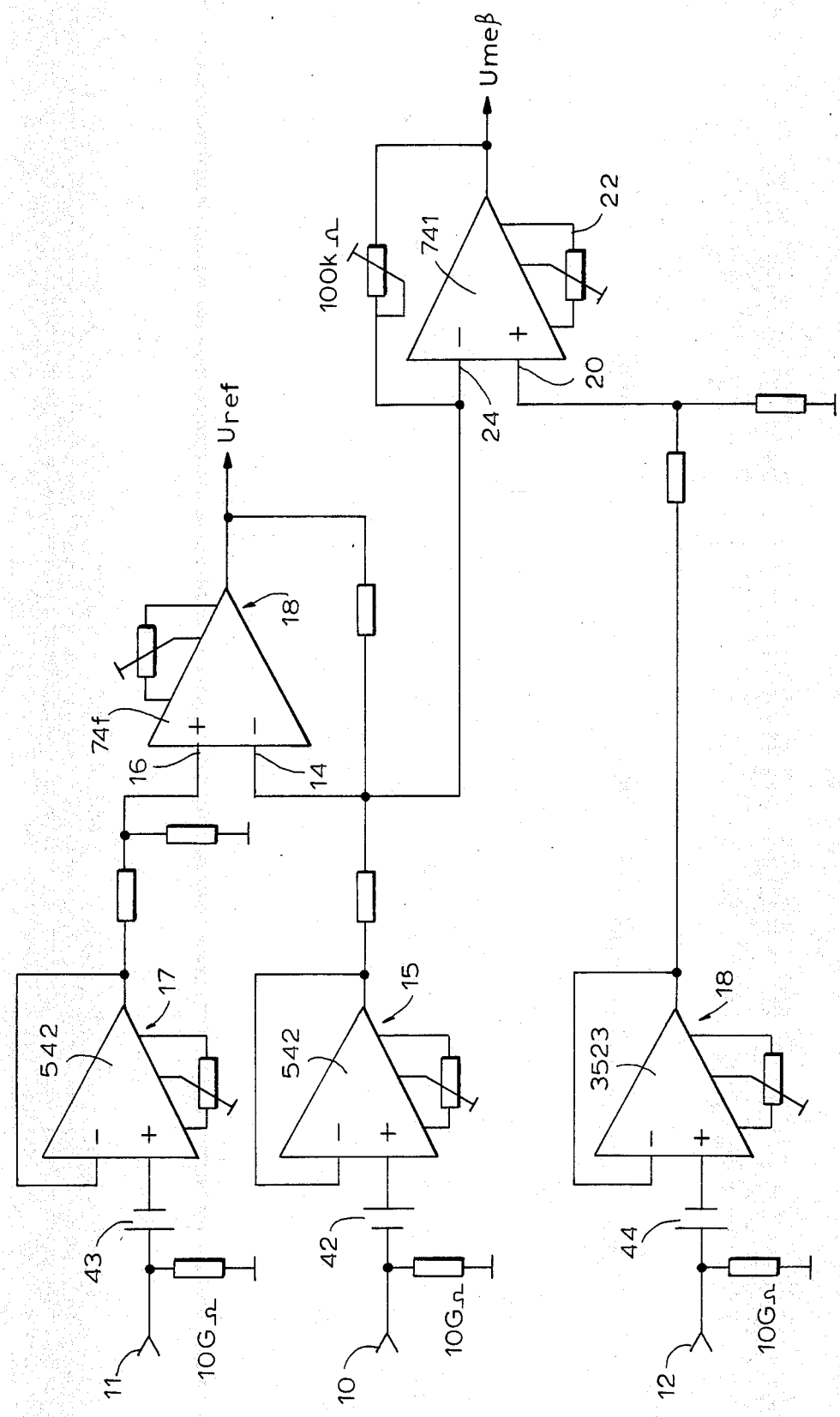

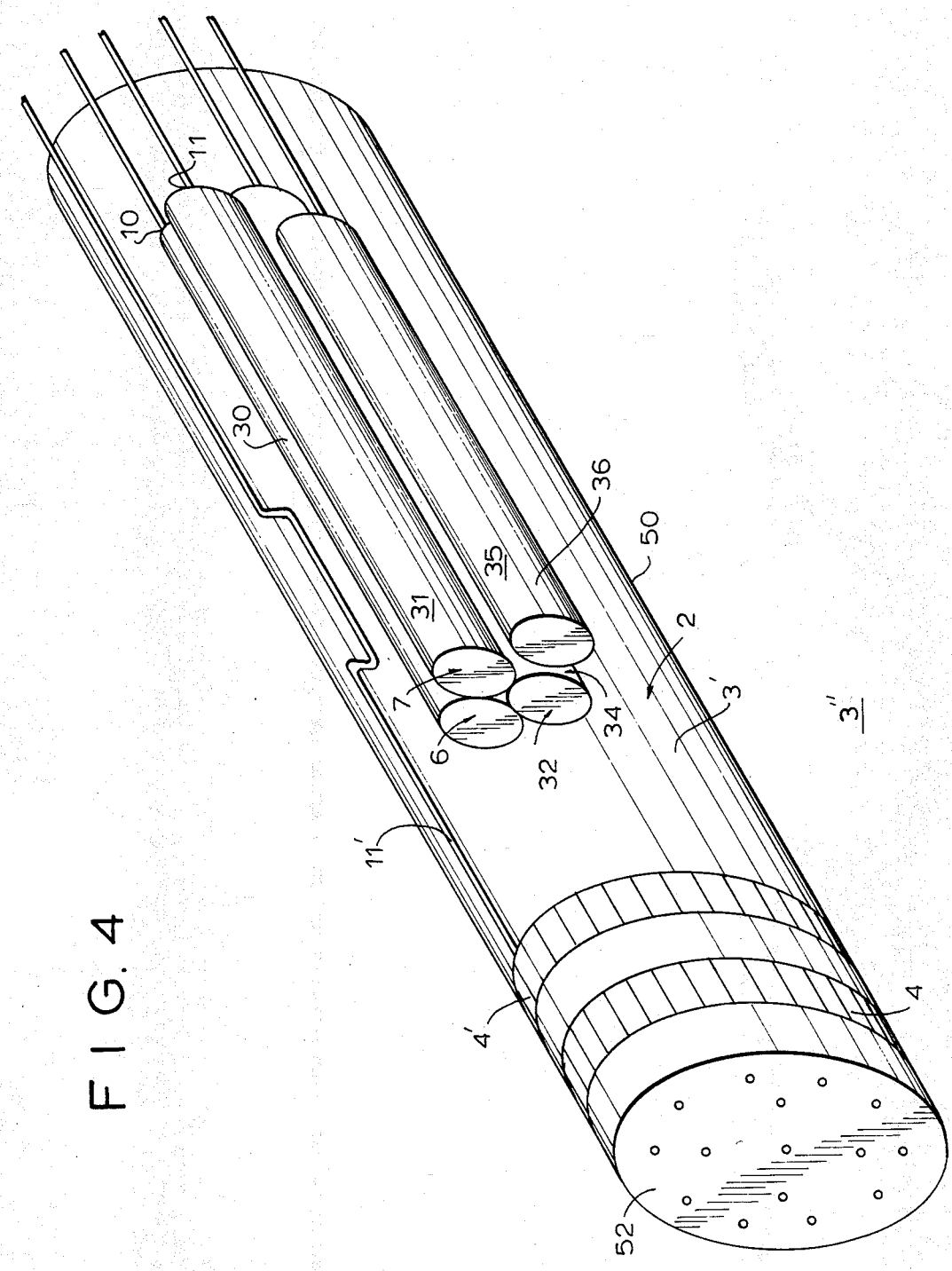

ARRANGEMENT FOR STABILIZING A GAS-REFERENCE ELECTRODE

BACKGROUND OF THE INVENTION

The present invention relates to an arrangement for stabilizing a gas-reference electrode used for electrochemical measurement of activities. In particular, the invention relates to an arrangement of the type which includes a reference electrode of nobel metal, a lipophile membrane partially covering the reference electrode and being arranged in a space which is filled with a hydrogen and oxygen containing electrolyte.

A device of this kind is known from EP-OS 0,141,178. The term "activities" denotes also fugacity corresponding to partial pressures of gas. The "partial covering" by the membrane indicates that the total reference electrode can be coated on its remaining or other parts by an insulating layer. In any event, the membrane serves for separating the electrode from the electrolyte in such a manner that the electrolyte is prevented from directly contacting any point of the electrode. The electric resistance of a metal reference electrode coated by a lipophile membrane is in the order of at least $10^9$ ohms.

Such reference electrodes are particularly suitable for use in the measuring devices inasmuch as due to the protective membrane whose further details are expressly referred to in the aforementioned EP-OS 0,141,178 application, have by themselves a high stability superior to prior reference electrodes. The present invention still improves the stability of such a gas-reference electrode. This further improvement is achieved by the provision of a source of gas for the gas-reference electrode.

The source of gas makes it possible to keep partial pressure of a specific gas for the reference electrode at a uniform level and consequently the measuring accuracy of the entire measuring arrangement in which the reference electrode is employed is increased. The gas source can be in the form for example of a flexible conduit from a gas reservoir. Preferably, also a suitable storage medium, such as $H_2$ storing metal sponge can be used.

In a preferred embodiment, the gas source includes an electrode, with advantage of a nobel metal, by means of which the gas needed for the reference electrode is released from the electrolyte. The gas source electrode together with the reference electrode are arranged in the electrolyte containing room. In this fashion a substantial reduction of size of the entire arrangement can be achieved. The direct supply of the gas always requires considerable space which particularly in physiological applications is not always available. By generating the measuring gas electrolytically in an electrolyte containing room a corresponding miniaturization of the arrangement is achievable.

With advantage, in the same electrolyte containing room which cooperates with a reference electrode there is also arranged a counter electrode for the gas releasing in the gas source. The gas generation takes place in its own electrolytic circuit consisting of the source electrode and of the counter electrode.

Of particular advantage is the provision of a source of a constant electrical current between the source electrode and the counter electrode to energize the gas source. In this manner, a constant gas generation is obtained by a simple electronic means and consequently a high measuring accuracy is guaranteed.

Gas-reference electrode arrangments are known. The reference electrodes are coupled via an electrolyte with a measuring electrode in which the concentration (that is the activity) of a substance under measurement varies. The corresponding voltage variations of the measuring electrode produced according to Nernst law are measured in conventional manner and employed as a measure for the activity (that is the concentration). For this purpose, the terminals of the measuring and reference electrodes are connected to corresponding inputs of a measuring instrument. As mentioned before, the "activities" mean also joint acidities corresponding to partial gas pressure.

An important condition for the accuracy of such a measurement is a sufficient stability, that is a constancy of the potential $E_o$ of the Nernst equation, that is particularly the constancy of the reference electrode. This potential value, however, depends substantially on conditions under which the gas-reference electrode operates, such as partial pressure of the employed gas and the temperature.

The reference electrode furthermore shows a certain drift which in contemplated applications, for example an implantation of the entire measuring arrangement in a human body, cannot be corrected by a recalibration. The drift is also independent of the constancy of the remaining operational conditions of the reference electrode. For example, the drift of a typical hydrogen reference electrode is in the order of 1 millivolt/5 days.

An objective of the invention is to provide an arrangement for stabilizing the gas-reference electrodes which in a simple manner guarantees a reliable stabilization of the reference potential on the electrode.

In a particularly preferred elaboration of this invention, the arrangement for the electro-chemical measurement of activities by means of a reference electrode of a nobel metal and a lipophile membrane partially covering the reference electrode, there is provided a further electrode of the same polarity as a measuring electrode, that means of a polarity which is opposite to the reference electrode to which a counter electrode serves as a source electrode whereby the terminal of the reference electrode is connected to an input of a difference amplifier and the terminal of the additional electrode is connected to another input of another difference amplifier whose output is measured.

It is been found that even in reliably operating reference electrodes, a certain drift frequently occurs in the course of time and the result of the entire arrangement of the measuring electrode and reference electrode can become incorrect. According to the invention, to avoid this drawback there is provided a further electrode of the polarity of the measuring electrode. The further electrode forms together with the reference electrode an electrochemical measuring system when the polarities of respective electrodes are opposite. Deviations occurring in this measuring system indicate an interference in the range of the reference electrode. The measured value of the system consisting of the measuring electrode and the reference electrode can in this event either disregard it or correct it according to the measuring result of the system reference electrode/further electrode. In doing so, it is of advantage to correlate the counter electrode of the source electrode for the reference electrode with the further electrode and to supply the same with the corresponding other amount of gas released from the electrolyte, so that the further electrode in addition to the result $U_{ref}$, contributes to the particular stability of the system reference electrode/further electrode.

Any fluctuations of the gas generation due to the interconnection of source electrode and counter electrode (which in turn is a source electrode for the further electrode) act in the same direction and consequently the effect of this interference is readily recognizable and correctable.

The terminal or electrical connection point of the first reference electrode is connected to an input of a difference amplifier whose other input is connected to the measuring electrode and to an input of another difference amplifier whose other input is connected to the terminal or electrical connection point of the second or further reference electrode. The output of the second difference amplifier $U_{ref}$ thus provides a measure for the relative changes between the first and second reference electrodes.

Since the current of the two gas source electrodes (that is source electrode for the first reference electrode and the counter electrode acting as a source electrode for the second reference electrode) is kept constant by the provision of an electric constant current source, any deviation can be safely traced to a failure in the electrode system, particularly in the reference electrode itself inasmuch it is improbable that such a failure would simultaneously and in the same direction occur both at the reference electrode and at the second reference electrode.

Preferably, the electric current between the source electrode and the counter electrode is monitored by a current measuring device. The output value of the measuring device can be employed for a suitable correction of the actual measured value derived from the comparison of the measuring electrode with the reference electrode.

The invention relates also to gas sources of the aforedescribed kinds. Such a gas source is preferably an electrolytical one and is arranged in the electrolyte containing room. On the other hand, it is required that the source be not impaired by the constituents and processes in an electrolyte. For this purpose, according to a feature of this invention, there is provided preferably a lipophile membrane between the source electrode and the electrolyte containing room, the membrane being permeable to gas and having preferably a proton carrier. Similarly as in the membrane pertaining to the reference electrode, the gas source membrane protects the gas source electrode against contact with electrolyte. As regards the particular construction of the membrane, reference is made to the German publication DE-OS 27 30 143 and to the EP-OS 0,141,178.

With advantage, an impedance convertor is connected between the connections of the first and second reference electrodes to the corresponding inputs of the differential amplifiers, thus enhancing ohmic resistance of the arrangement. To obtain a high measuring accuracy, the overall arrangement of the reference electrodes and of the measuring electrode is designed with high resistance so that a potentiometric mode of operation would be possible. The corresponding currents are in the order of $10^{-15}$ amperes. Such minute currents are achievable particularly by additional measures using further membranes as it will be explained in greater detail below.

The high ohmic resistance of the reference electrode is also adjusted by suitable measures on the measuring electrodes so that the measuring differential amplifier can suppress noise.

In a preferred embodiment, the reference electrode is a hydrogen electrode and the additional or second electrode is an oxygen electrode. These electrode types have been particularly successful in contemplated application fields. When the reference electrode is a hydrogen electrode (connected and acting as an anode) it is possible to measure on the corresponding measuring electrode the $O_2$ gas and numerous cations such as for example $K^+$, $Na^+$. Such an overall arrangement with an oxygen electrode described for example in DE-OS 27 30 143, is preferred too.

Alternatively, a reference electrode as an oxygen electrode is also of preference. The oxygen electrodes are employed with advantage as reference electrodes in measuring certain substances. The further electrode in this case is a hydrogen electrode. The appropriate measuring electrode can measure gases (for example $H_2$, see the copending German paten application P 35 37 915.4 of the same priority date and of the same inventors) and $H_2O_2$ (see the aforementioned EP-OS 0,141,178). The corresponding measuring electrode then is able to measure further anions, such as for example $Cl^-$ or $HCO_3^-$. For this purpose membranes with suitable carriers are used.

In any event the reference electrodes are gas electrodes, since in this case the generation and discharge of the required gas is particularly simple.

Gold electrodes have been found as particularly successful for the gas-reference electrodes and further electrodes inasmuch as those can be easily and reliably applied by sputtering on the membranes. Alternavitely, platinum electrodes or other nobel metals are applicable.

In another preferred embodiment of this invention, the reference electrode and/or the further electrode is made of palladium plated platinum.

In a preferred embodiment of this invention, a protective membrane is provided between the electrolyte and the reference electrode and between the electrolyte and the other electrode. As mentioned before, the protective membrane protects the electrodes against contact with the electrolyte. This arrangement of protective membranes substantially improves the stability of the reference electrode and contributes together with other measures to the high ohmic resistance and minute currents in the potentiometric measurement. The high stability of the electrodes results particularly from the fact that any pollution of the electrodes by substances which do not participate in the reaction is effectively avoided. Such protective membranes are described in detail in the aforementioned EP-OS 0.141,178. Also, in the case of protective membranes a lipophile membrane provided with a proton carrier is preferred.

In a preferred embodiment of the arrangement of this invention, a hydrogen source for the reference electrode is used. The hydrogen source creates particularly uniform conditions for the reference electrode.

In the case of an oxygen-reference electrode, the arrangement is provided with a corresponding oxygen source.

The further electrode has always a source for the other gas.

This invention refers also to an electrolytic catheter- or tubular needle measuring device having elongated housing in the form of a hollow cylinder in which the measuring- and/or reference electrodes as well as further electrodes are arranged. The measuring and reference electrodes as well as the optional further electrodes are designed with the before described features and their combinations.

The measuring devices designed in accordance with this invention have the advantage of a convenient application in physiological measurements, particular in vivo. As a rule, for such measurements extremely minute amounts of substances to be measured are available whereby a high accuracy of measurement is required on the one hand and a specific adjustment to particular measuring circumstances is needed on the other hand. The measuring devices of this invention are particularly suitable for insertion in human body.

The adjustability of this invention for measurements in the human body is achieved by accommodating the reference electrode or the further electrode in the interior of a measuring cylinder, the electrodes being in the form of wires which are arranged parallel one to another in axial direction of the cylinder. In this manner it is made possible to accommodate in a compact and space saving fashion the electrodes in a catheter or hollow needle. It is still possible to provide the wires with the membranes, for example by enveloping and connect the same to the appropriate electronic circuits.

If desired in combination with the before described features, the measuring electrodes have a substantially annular configuration and are situated on the outer surface of the jacket of the hollow cylinder. In this manner, the measuring electrode is for example in the form of a flat band applied on the cylinder by a vaporing or sputtering process and are brought immediately in contact with the physiological solutions for example with tissue liquids in tissues in which the hollow needle is introduced.

It is of advantage to provide a leading opening of a hollow cylinder with an ion permeable (preferably a porous) membrane which closes the interior of the cylinder from the environment. By virtue of these measures it is made possible to adjust the electrolyte of the measuring device, for example to the values of blood. In this case it suffices to employ a simple porous membrane for separating the electrolyte and the measuring liquid one from the other. Due to the high ohmic resistance of the measuring arrangement of this invention, the deposits of proteins do not interfere by an impedance increase since they increase the overall high impedance only insignificantly. In contrast, the membrane prevents the contamination of the inner space of the hollow needle.

Preferably, the inner space of the hollow cylinder is filled with an electrolyte. The latter is adjusted to the solution to be measured provided it is not operated enzymatically (see for example the before mentioned EP-OS 1,141,178).

In the preferred embodiment of this invention the gas generating electrodes are in the form of wires. In this manner they can be easily accommodated in the interior of the measuring device. Preferred embodiments of respective electrodes will be explained below.

In a preferred embodiment of this invention, there are provided two measuring electrodes of which one is designed as an anodic and the other as a cathodic electrode. The terms "anodic (or cathodic) design" means that the electrode by virtue of its design, its material and its polarization voltage acts as an anode or a cathode relative to the reference electrode. The reference electrodes are constructed to match the measuring electrodes.

In the follow description, specific embodiments of this invention will be explained in connection with the accompanying drawing, in which FIG. 1 shows schematically an arrangement of a reference electrode and a gas source electrode in accordance with this invention;

FIG. 3 is a diagram of a circuit for controlling a reference electrode and a measuring electrode and a further electrode; and FIG. 4 is a perspective view of a cutaway part of a catheter type measuring device.

DESCRIPTION OF THE PREFERRED EMBODIMENTS

Figure 2:
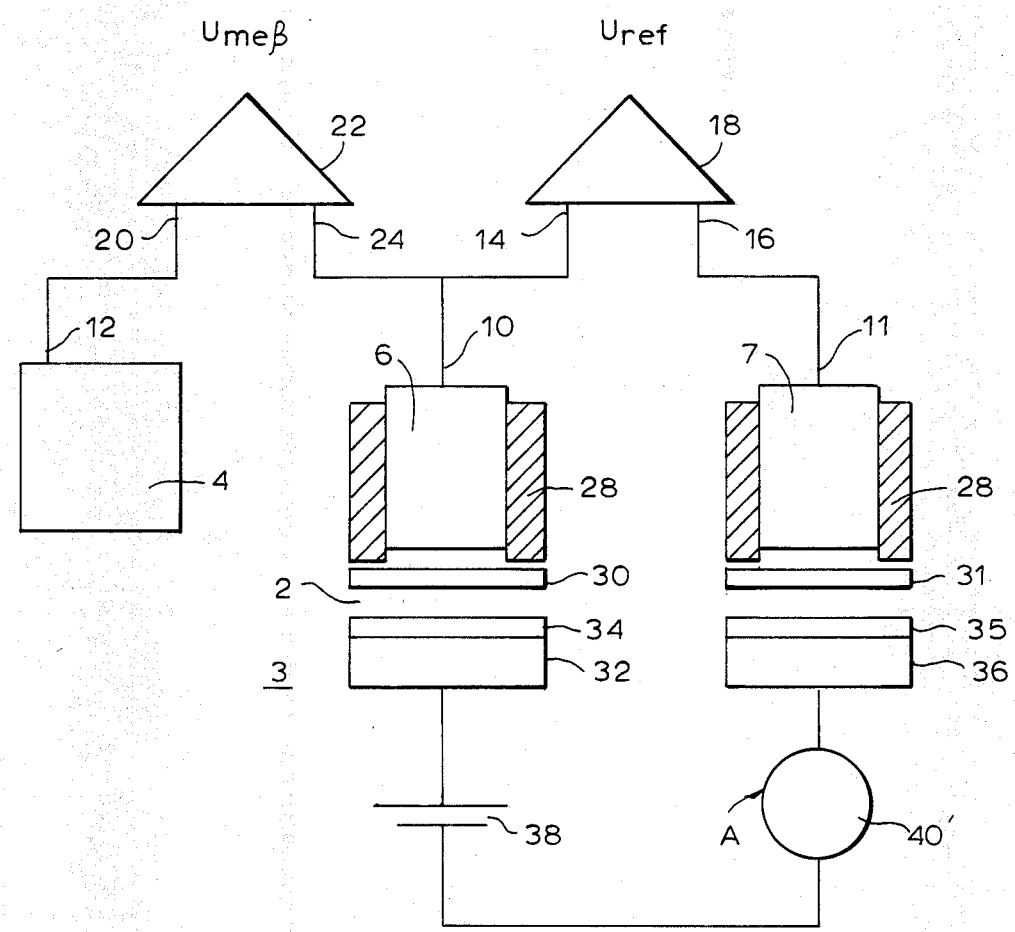
FIG. 2 is a block circuit diagram of a reference electrode connected to a further reference electrode and cooperating with gas generating sources.

A hydrogen reference electrode 6 made of gold is coated on its major surface portion with an insulating layer 28 whereas a lower surface portion is covered by a lipophile membrane 30 with a proton carrier. The membrane 30 separates the electrode 6 from an electrolyte 2 containing hydrogen and oxygen and filling a space indicated by reference numeral 3. A hydrogen source 32 is arranged in the electrolyte space or room 3 opposite the membrane 30. The hydrogen source 32, in order to provide a uniform supply of hydrogen, is separated from the electrolyte 2 by another lipophile membrane 34. In a modification, the other membrane can be made of PVC. A counter electrode 36 for a hydrogen generating electrode constituting the gas source 32, is an oxygen generating electrode and is coupled via a suitably poled or polarized DC voltage source 38 to the hydrogen generating electrodes 32. A constant current source 40 is connected in the circuit of the electrodes 32 and 36 to keep a constant current I flowing through the circuit. Due to the constant current I, the hydrogen is released from the electrolyte at a uniform rate, in this example with a partial pressure of 1 millimeter Hg. Under such condition the detrimental affect of hydrogen on the electrodes is reduced.

In the embodiment of FIG. 2, the arrangement of this invention includes the reference electrode 6 and a further electrode 7 and a measuring electrode 4. The measuring electrode 4, in this example a cathode, and the reference electrode 6, in this example an anode and the further electrode 7, in this example again a cathode, are located in space 3 containing the electrolyte 2. The electrodes 6 and 7 are again partially coated by an insulating layer 28 and 29' and partially covered by the membranes 30 and 31. The upper uncoated part of the electrodes 6 and 7 serves as an electrical terminal or connection point.

Sources of polarizing voltages required for the gas electrodes are not illustrated in FIG. 2 but are shown in FIG. 3.

The electrical terminal 10 of reference electrode 6 is connected to an input 24 of a difference amplifier 22 and to an input 14 of another difference amplifier 18. The electrical terminal 11 of the further electrode 7 is connected to another input 16 of the difference amplifier 18 whereas the electrical terminal 12 of the measuring electrode 4 is connected to another input 20 of the measuring difference amplifier 22.

It will be seen from FIG. 2, that each of the electrodes 6 and 7 faces an assigned gas source 32 and 36 of which the gas source 32 releases hydrogen and the gas source 36 releases oxygen. The lateral sides of respective electrodes 6 and 7 are protected, in this example by PVC layers 28 and 28'. Lower surfaces of respective electrodes which are not coated by the PVC layers and which are surrounded by the electrolyte 2, are covered respectively by a lipophile protective membrane 30 or 31, which may be of PVC. The membrane separate the electrodes from the electrolyte 2. Each of the membrane 30 and 31 contains a proton carrier which makes them permeable to protons. The gas sources will be explained in connection with the embodiment of FIG. 1. The protective membranes 34 and 35 are made permeable to gas generated by the assigned gas releasing electrode and to ions which generate the gas, or are provided with suitable carriers. In FIG. 2, a current measuring instrument 40' is illustrated which monitors the current flow and hence the gas generation.

FIG. 3 shows in greater detail the control circuits for the electrodes. The type numbers of respective component parts are those of the firm Analogue Devices. The value of blank resistors is 10 kilo-ohms. The power supply is $\pm$- eight volts blocked by 2.2 $\mu$F. Parts corresponding to those in FIGS. 1 and 2 are denoted by like reference numerals.

The electrical terminal 10 of a nonillustrated reference electrode 6 is applied via a source of polarizing voltage 42 (of 150 millivolts for example) to the positive input of an impedance convertor 15.

The output of the impedance convertor is fed back to its negative input and is further connected via a resistor to the negative input 14 of the difference amplifier 18. The output of the amplifier 18 is fed back via a resistor to its negative input 14. The output terminal 10 of the reference electrode 6 before the voltage source 42 is connected to ground by a high resistor of 10 G ohms which lowers impedance relative to a value which would be delivered by the impedance convertor by itself.

The connection between the electrical terminal 11 of the further electrode 7 and the positive input 16 of the difference amplifier is identical to that of the connection of the terminal 10. The positive terminal 16 of the amplifier 18 is connected to ground via a resistor.

The output of the difference amplifier 18 delivers a signal yielding an information about instability or drift of the reference electrode 6.

The output of a measuring difference amplifier 22 (which measures the difference between the voltages of the measuring electrode 4 and reference electrode 6) is fed back via an adjustable resistor 100 Kilo-ohms to its negative input 24 and the output voltage $U_{mes}$ at the output of amplifier 22 indicates the change of potential at the measuring electrode 4.

The output of the impedance convertor 15 is connected via a resistor both to the negative input 14 of the difference amplifier 18 and to the negative input 24 of the measuring difference amplifier 22.

The electrical terminal 12 of the measuring electrode 4 is grounded via a resistor of 10 G ohms and is applied via a source of polarizing voltage 44 of about 300 millivolts to the positive input of an operational amplifier 19 whose output is connected with its negative input. The output of the amplifier 19 is further connected via a resistor with the positive input 20 of the measuring difference amplifier 22 and the positive input 20 is grounded via a resistor.

At the potentiometric measurement whose high stability is made possible by the before described membranes, due to the high impedance extremely small currents in the order of $10^{-15}$ amperes flow through the circuit.

Referring now to FIG. 4, the illustrated measuring device includes a hollow cylinder 50 which according to its dimensions can be used as a catheter, hollow needle or a puncture electrode. The front opening of the hollow cylinder is closed by an ion permeable porous membrane 52 of a conventional design. At the front end region of the jacket of the cylinder, in the proximity of the porous membrane 52, are provided one after the other in the following order $pO_2$ measuring electrode 4 which as described before is designed and connected as a cathode, followed by $pH_2$ or $H_2O_2$ - measuring electrode 4'. In the interior 3' of the hollow cylinder 50 an inner electrolyte 2 is present which establishes via the pores of the membrane 52 an electrolytic connection for example with the tissue liquid being measured and consequently with the outer measuring electrodes 4 and 4'. The inner electrolyte 2 as mentioned before, by using gas electrodes and especially by using the membranes, can process a mol strength corresponding blood values. In this case, no diffusion potential occurs. A precipitate from blood which might clog the pores of the membrane is thus effectively avoided.

In the interior of the hollow cylinders there are arranged in an axially parallel position four wires of nobel metal which over a certain surface range are coated with a lipophile carrier membrane. The wire 32 with the membrane coating 34 serves as an electrolytic hydrogen generator and the wire 36 with the membrane 35 serves as an electrolytic oxygen generator. The wires 6 and 7 act respectively as a gas reference electrode and a further electrode which in this example are designed as a hydrogen anode and an oxygen cathode and are coated respectively by membranes 30 and 31. The wires are electrically connected at the uncoated end thereof to insulated cables 10 and 11.

The annular measuring electrodes 4 and 4' are also connected to insulated cables of which cable 11' is shown and all the cable pass through the tubular housing 50 to an outside connector.

This illustrated embodiment of the arrangement of the electrodes in the form of axial parallel wires is particularly advantageous because it produces the desired results without any detrimental side effects.

The inventive arrangement makes it further possible by suitable connections and disconnections of respective electrodes to perform either an anodic measurement (electrode 4') or a cathodic measurement (electrode 4) or both together.

Normally the illustrated electrodes are electrically interconnected by the circuits described in connection with Figs. 2 and 3.

What we claim is:

1. An arrangement for stabilizing a gas-reference electrode in a device for measuring electrochemical activities in a hydrogen and oxygen containing electrolyte present in a space, comprising a reference electrode of a nobel metal; a lipophile membrane covering a surface portion of the reference electrode and being arranged in said space to contact said electrolyte; a source of gas arranged in said space opposite said reference electrode to supply gas toward the same, said gas source including a source electrode of a nobel metal, which is in contact with said electrolyte to release the gas there-from; and another lipophile membrane covering at least a surface portion of said source electrode opposite said first mentioned lipophile membrane, said other lipophile membrane being permeable to the gas released from the electrolyte by the action of the source electrode and being in contact with the electrolyte.

2. An arrangement as defined in claim 1; and further comprising a counter electrode arranged in said space in contact with the electrolyte and being electrically coupled to said source electrode.

3. An arrangement as defined in claim 2, comprising a source of a constant electrical current connected between said source electrode and said counter electrode to produce a constant current path through said electrolyte.

4. An arrangement as defined in claim 3, wherein said measuring device includes a measuring electrode connected to a DC voltage source of one polarity, a further electrode connected to a DC voltage source of the same one polarity, said gas reference electrode being connected to a DC voltage source of an opposite polarity, said counter electrode acting as a source electrode for said further electrode, and including a control circuit comprising first difference amplifier whose one input is connected to the measuring electrode and whose other input is connected to the gas reference electrode, and a second difference amplifier whose one input is connected to the gas reference electrode and whose other input is connected to the further electrode whereby the output of the second difference amplifier generates a reference signal.

5. An arrangement as defined in claim 4, wherein a current measuring device is arranged between the source electrode and the counter electrode.

6. An arrangement as defined in claim 5, wherein said electrical control circuit further includes impedance means connected respectively between said gas reference electrode, said measuring electrode, said further electrode and the inputs of said difference amplifiers so as to increase impedance of the entire measuring device.

7. An arrangement as defined in claim 6, wherein the gas reference electrode is designed as a hydrogen electrode and the further electrode is designed as an oxygen electrode.

8. An arrangement as defined in claim 6, wherein the gas reference electrode is designed as an oxygen electrode and the further electrode is designed as a hydrogen electrode.

9. An arrangement as defined in claim 6, wherein the gas reference electrode and the further electrode are made of a nobel metal.

10. An arrangement as defined in claim 9, wherein the gas reference and the further electrode are made of palladium plated platinum.

11. An arrangement as defined in claim 9 wherein said nobel metal is gold.

12. An arrangement as defined in claim 9 wherein said nobel metal is platinum.

13. An arrangement as defined in claim 4, wherein the further electrode is covered by a lipophile protective membrane.

14. An arrangement as defined in claim 13, wherein the lipophile membrane of the further electrode includes proton carrier molecules.

15. An arrangement as defined in claim 14, wherein the counter electrode serving as a source electrode for the further electrode is covered by a lipophile protective membrane.

16. An arrangement as defined in claim 1, wherein the gas source for the reference electrode is a hydrogen gas source.

17. An arrangement as defined in claim 1, wherein the gas source for the reference electrode is an oxygen gas source.

18. An arrangement as defined in claim 1 wherein said lipophile membranes include proton carrier molecules.

19. An electrolytic catheter or a hollow needle measuring device including a measuring electrode, a gas reference electrode, a further electrode and a gas source electrode, said electrodes being partially coated with a lipophile membrane, comprising an elongated housing in the form of a hollow cylinder, said electrodes being in the form of nobel metal wires arranged in axially parallel relation within said cylindrical housing.

20. An electrolytic catheter or a hollow needle measuring device comprising an elongated housing in the form of a hollow cylinder, a gas reference electrode, a further electrode, a gas source electrode and a counter electrode acting as a gas source electrode for the further electrode, said electrodes being in the form of of nobel metal wires, arranged axially parallel in said housing and being coated by a lipophile membrane, and further comprising at least one annular measuring electrode arranged on the upper surface of said cylindrical housing, said electrodes being connected via insulated cables passing through the housing to an electronic control circuit.

21. A measuring device as defined in claim 20, wherein said hollow cylindrical housing is closed at one end thereof by an ion permeable membrane.

22. A measuring device as defined in claim 21, wherein the interior of said hollow cylindrical housing is filled with an electrolyte which is in contact with said lipophile membranes.

23. A measuring device as defined in claim 22, wherein said source electrode and said counter electrode are arranged respectively opposite said gas reference electrode and said further electrode, and said electrodes being in the form of axially parallel wires.

24. A measuring device as defined in claim 22, comprising two annular measuring electrodes arranged one after the other at an inlet end of the hollow cylindrical housing, one of said measuring electrodes being designed as an anode and the other measuring electrode being designed as a cathode.

* * * * *